(12) United States Patent
Fanta et al.

(10) Patent No.: US 6,294,289 B1
(45) Date of Patent: Sep. 25, 2001

(54) CYANO-SUBSTITUTED METHIDE AND AMIDE SALTS

(75) Inventors: Alan David Fanta, Minneapolis; Phat tan Pham, Little Canada; William Mario Lamanna, Stillwater, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/139,315

(22) Filed: Aug. 25, 1998

(51) Int. Cl.$^7$ ..................................................... H01M 6/04
(52) U.S. Cl. ........................ 429/188; 558/437; 558/439; 534/735; 568/31; 429/122; 429/128; 429/232
(58) Field of Search ...................................... 558/437, 439; 534/735; 568/31; 429/122, 128, 188, 232

(56) References Cited

U.S. PATENT DOCUMENTS

| | | |
|---|---|---|
| 5,232,940 | 8/1993 | Hatton et al. . |
| 5,273,840 | 12/1993 | Dominey . |
| 5,446,134 | 8/1995 | Armand et al. . |

FOREIGN PATENT DOCUMENTS

| | | |
|---|---|---|
| 118433 | 3/1976 | (DE) . |
| 3545594 | 6/1987 | (DE) . |
| 0 850 920 A2 | 1/1998 | (EP) . |
| 0 850 921 A1 | 1/1998 | (EP) . |
| 850920 | 7/1998 | (EP) . |
| 850921 | 7/1998 | (EP) . |

OTHER PUBLICATIONS

A. Dornow et al., "Uber Die Verwendung Von a–Ketonitrilen", Chem. Ber. vol. 91, 1958 (with Chem. Abst. English Abstract).

L. Jager et al., "ESCA–Spektren einiger Dicyanmethanido– und Cyanamido–sulfonate bzw.–carboxylate der Typen M[RSO$_2$C(CN)$_2$], M[RSO$_2$NCN] und M[RC(O)NCN]", Z. anorg. allg. Chem. 605 (1991), pp. 125–129 (English Abstract).

Ilmar A. Koppel et al., "The Gas–Phase Acidities of Very Strong Neutral Bronsted Acids", J. Am. Chem. Soc. 1994, 116, 3047–3057.

V. I. Krokhtyak et al., "Synthesis and Transformations of 1–Cyano–2–Chlorethylenes with Perfluoroalkyl and Trifluoromethylthio Groups", Institute of Organic Chemistry, Academy of Sciences of the Ukrainian SSR, Kiev; translated from Zhurnal Organicheskoi Khimii, vol. 17, No. 2, pp. 268–272, Feb. 1981; original article submitted Jul. 30, 1980.

Herbert W. Roesky et al., "Synthese und Struktur des Trifluoracetyldicyanomethanids", Z. Naturforsch, 40b, 883–885 (1985); Mar. 7, 1985.

Wang et al., "Design and Synthesis of a Perfluoroalkyldicyanovinyl–Based NLO Material for Electro–Optic Applications," Polymer Preprints, vol. 38, No. 1, pp. 971–972 (1997).

Yagupolskii et al., "Trifluoromethylsulphonylmethanides Functionalized by a CN Group," Heteroatom Chemistry, vol. 9, No. 6, pp. 565–570 (1998).

*Primary Examiner*—Samuel A. Acquah
(74) *Attorney, Agent, or Firm*—Daniel C. Schulte; Robert H. Jordan

(57) ABSTRACT

Amide and methide salts, comprising in the case of an amide salt one cyano (—CN) group, and in the case of a methide salt, two cyano groups are described in applications requiring a high degree of ionic dissociation. The salts are especially useful as electrolyte components in electrochemical cells such as batteries, fuel cells, capacitors, supercapacitors, electrochemical sensors and electrolytic cells, by providing a means for ionic conduction and transport.

11 Claims, No Drawings

CYANO-SUBSTITUTED METHIDE AND AMIDE SALTS

FIELD OF THE INVENTION

This invention relates to cyano-substituted salts including cyano-substituted methides and amides.

BACKGROUND OF THE INVENTION

Industry is continually searching for new weakly coordinating anions which form highly dissociating salts. Such salts can often be useful as conductivity additives or enhancers, when dissolved or dispensed in other materials; as cationic polymerization initiators or catalysts; as antistatic additives; as surfactants; and often, in combination with other materials, can be used to conduct electrical charge, for example, as electrolytes (ionic conductors) within electrochemical cells such as batteries, fuel cells, capacitors, supercapacitors and electrochemical sensors, etc.

Of course these salts should exhibit specific chemical and physical properties to be useful in such applications. First of all they must exhibit good ionic conductivity. In many applications they must also exhibit thermal and electrochemical stability. They should not cause damage to other components of systems in which they are used (e.g., corrosion). They should have acceptable environmental impact; and, they preferably can be produced at an economically feasible price. When employed in electrochemical cells the salts should exhibit good cycling properties and should produce electrochemical cells that can be operated and maintained with minimal concerns for safety.

With respect to the very specific application of salt compounds in electrochemical cells, there is both a current and projected future demand for high energy density, lightweight, rechargeable power sources for use in automotive, industrial, and consumer markets. Many of these needs can potentially be met by lithium-ion battery technology, which requires the use of electrolyte salts dissolved in a non-aqueous solvent to act as an electrolyte. This electrolyte solution acts as the medium in which ionic conduction can occur between electrodes, providing charge balance within an electrochemical cell, such as a battery.

There are currently only a small number of electrolyte salts known to be suitable for use in lithium-ion batteries, and all have identifiable drawbacks. The most common electrolyte salt is $LiPF_6$, which exhibits good conductivity and corrosion resistance, but is thermally and hydrolytically unstable. Hydrolytically unstable means that exposure to water will cause decomposition to form fluoride ions. Other salts having potential uses as lithium electrolytes include $LiAsF_6$ (toxic), $LiBF_4$ (relatively poor conductivity), and $LiClO_4$ (potentially explosive). There are also a number of known organofluorine lithium salts, but each of these has its own individual short-comings. Molecules like $LiOSO_2CF_3$ and $LiN(SO_2CF_3)_2$ are thermally very stable but can be corrosive to aluminum current collectors, and $LiC(SO_2CF_3)_3$ is expensive to produce for most commercial scale applications.

The battery industry is currently seeking electrolyte salts which can perform at useful conductivity levels, and that are easily handled and can be produced at a reasonable cost.

SUMMARY OF THE INVENTION

Amide and methide salts, including in the case of an amide salt one cyano (—CN) group, and in the case of a methide salt, two cyano groups, have been found useful in applications requiring a high degree of ionic dissociation. The salts are especially useful as electrolyte components in electrochemical cells such as batteries, fuel cells, capacitors, supercapacitors, electrochemical sensors and electrolytic cells, by providing a means for ionic conduction and transport.

Accordingly, the present invention relates to an electrolyte which includes a salt of an N-cyano-substituted amide, (e.g., an N-cyano-substituted carboxamide, or an N-cyano-substituted sulfonamide), a dicyano-substituted sulfonyl methide, a dicyanoacyl methide, or a mixture thereof in a matrix material.

More specifically, the present invention includes as an electrolyte a matrix material and a salt of the formula

$$R—[Q—X^-(CN)_n]_y y/m M^{m+} \quad (I)$$

wherein y is 1 or 2;

X is C or N, which when X is C, n is 2 and when X is N, n is 1;

R is a fluorine atom, a hydrocarbon or a fluorinated hydrocarbon group;

Q is a linking group; and $M^{m+}$ is a cation having a valence of m. A mixture of salts of formula I may also be included in the electrolyte.

Another aspect of the present invention is an electrochemical cell containing the above described electrolyte, an anode and a cathode.

A further aspect of the present invention includes certain novel methide and amide salts which are salts of an N-cyano-substituted amide, (e.g., an N-cyano-substituted carboxamide or an N-cyano-substituted sulfonamide), a dicyano-substituted sulfonyl methide, or a dicyanoacyl methide.

More specifically, novel salts of the invention include methide salts of the formula

$$R—[SO_2—C^-(CN)_2]_y y/m M^{m+} \quad (II)$$

wherein y is 1 or 2;

R is a fluorine atom or a perfluorinated hydrocarbon group; and $M^{m+}$ is a cation having a valence of m.

Novel salts of the invention also include amide salts of the formula

$$R—[Q—N^-CN]_y y/m M^{m+} \quad (III)$$

wherein y is 1 or 2;

R is a fluorine atom or a perfluorinated hydrocarbon group;

Q is a linking group; and $M^{m+}$ is a cation having a valence of m.

Further salts include salts containing polymerizable groups, for example, methide salts of the formula

$$R—[Q—C^-(CN)_2]_y y/m M^{m+} \quad (IV)$$

wherein y is 1 or 2;

R is a halogenated or non-halogenated polymerizable group;

Q is a linking group; and $M^{m+}$ is a cation having a valence of m; and amide salts of the formula $$R-[SO_2-N^-CN]_y/mM^{m+} \qquad (V)$$

wherein y is 1 or 2;
R is a halogenated or non-halogenated polymerizable group; and
$M^{m+}$ is a cation having a valence of m.

DETAILED DESCRIPTION

Definitions

Throughout this application the following definitions apply:

"Electrochemical cell" includes all electrical energy storage devices and electrolytic cells, including capacitors, supercapacitors, electrochromic devices, electrochemical sensors, fuel cells and batteries.

"Macromolecular material" refers to a homopolymer, copolymer, or combination thereof, which may or may not be cross-linked and/or plasticized.

"Gel" refers to a physically or chemically cross-linked polymer swollen with solvent.

"Matrix" or "matrix material" refers to a medium (e.g., a solid, liquid, gel or plasticized polymer) in which electrolyte salts may be dissolved or dispersed to form an ionically conductive electrolyte. For a "lithium ion battery," the matrix is liquid; for a "lithium polymer battery," the matrix is a solid, gel or plasticized polymer.

"Plasticized polymer" refers to a polymer containing a low molecular weight additive, such as an organic solvent.

Voltages specified refer to electrical potential differences between a positive electrode measured relative to a $Li/Li^+$ reference electrode, except where otherwise noted.

A fluorocarbon group may be either a partially or fully fluorinated (i.e., perfluorinated) hydrocarbon chain. A partially fluorinated hydrocarbon chain exists where only a portion of the hydrogen atoms in the hydrocarbon has been replaced by fluorine atoms. In a fully fluorinated or perfluorinated hydrocarbon chain, essentially all of the hydrogen atoms, e.g. at least 90%, attached to carbon have been replaced by fluorine. Thus, the non-skeletal valence bonds are preferably carbon-to-fluorine bonds. However, an occasional carbon bonded hydrogen atom, bromine atom or chlorine atom may be present in a fully fluorinated hydrocarbon chain.

A "hydrocarbon group" refers to a monovalent or divalent straight or branched aliphatic group, a cycloaliphatic group, a cycloaliphatic-aliphatic group, or an aryl, biaryl or aralkyl group. These groups are further defined below.

"A straight or branched aliphatic group" refers to a hydrocarbon radical, e.g. an alkyl group, which is either in the form of a straight or branched chain and, in this case, ranging from 1 to 18 carbon atoms or as otherwise designated.

"Cycloaliphatic group" is a cyclic group, e.g. a cycloalkyl group, having from 3 to 12 carbon atoms and refers to a cyclic saturated group. Thus, the group includes, for example, cyclopropyl, cyclobutyl, cyclopentyl, cyclohexyl, and the like.

"Alkylene" refers to either straight or branched chain divalent organic groups which may join at both ends to another group or groups. Preferred alkylene groups are ethylene and propylene.

"Acyl" refers to either a straight, branched or cyclic hydrocarbon group which has a carbonyl group, such as an alkanoyl group, e.g. acetyl, or aroyl, e.g. benzoyl.

"Fluorinated divalent hydrocarbon" refers to either straight or branched chain divalent partially fluorinated organic groups which may join at both ends to another group or groups, such as a "fluoroalkylene" group, e.g. fluoroethylene, fluoropropylene and fluorobutylene.

The term "aryl" refers to a substituted or unsubstituted aromatic hydrocarbon, preferably a phenyl or naphthyl group which is unsubstituted or substituted by well recognized aromatic substituents such as, for example, alkyl of 1–4 carbon atoms, The term "reactive groups" includes any group capable of reacting with itself or with other groups. For example, R can contain a polymerizable group such as an olefinically unsaturated group (e.g., acrylate or allyl), an epoxide group, an isocyanato group and the like that would allow the amide or methide salt to react with other reactive compounds, including other molecules of the same salt or molecules of a different reactive or polymerizable compound, via grafting or polymerization (cationic, anionic or free radical mechanism) to form a homopolymer or a copolymer. Such a homopolymer or copolymer material would be useful in electrolytes, particularly as single ion conductors. The above polymerizable groups include halogenated or non-halogenated groups where the halogenated group preferably contains fluorine atoms as the halogen.

"A heteroatom" refers to a heteroatom interrupting a carbon chain, such as for example nitrogen, oxygen, or sulfur.

Electrolytes

An electrolyte is defined as a salt or a combination of salts in a matrix, the matrix being preferably a non-aqueous solvent. The invention is an electrolyte which contains a salt selected from the group consisting of N-cyano-substituted amide (e.g., a N-cyano-substituted carboxamide, or N-cyano-substituted sulfonamide), a dicyano-substituted sulfonylmethide, a dicyanoacyl methide and a matrix material.

More generally, the invention is an electrolyte that contains a salt of the formula:

$$R-[Q-X^-(CN)_n]_y/mM^{m+} \qquad (I)$$

and a matrix material; wherein y is 1 or 2, and X is C or N. When X is C, n is 2 and the compound is a methide. When X is N, n is 1 and the compound is an amide.

In the electrolyte salts of formula I, Q is a linking group selected from $-SO_2-$ and $-C(O)-$ and $M^{m+}$ is a cation having a valence of m.

Suitable cations, $M^{m+}$, include alkali metal cations (e.g., $Li^+$, $Na^+$, $K^+$ and $Cs^+$), alkaline earth metal cations (e.g., $Mg^{2+}$, $Ca^{2+}$, $Sr^{2+}$ and $Ba^{2+}$), Group IIIA cations (e.g., $Al^{3+}$), transition metal cations (e.g., $Fe^{3+}$, $Fe^{2+}$, $Zn^{2+}$, $Ti^{4+}$ and $Cu^{2+}$), rare earth metal cations (e.g., $Ce^{4+}$ and $La^{3+}$), alkylammonium cations (i.e., $R_4N^+$, where R is independently alkyl, preferably having from 1 to 4 carbon atoms, aryl or hydrogen), sulfonium cations (i.e., $R_3S^+$), iodonium cations (i.e., $R_2I^+$), phosphonium cations (i.e., $R_4P^+$) and protons (i.e., $H^+$). Suitable cations also include organometallic cations such as ferrocenium cation, cyclopentadienyl (arene) $M^{m+}$, $(arene)M(CO)_3^{m+}$, $(arene)_2M^{m+}$ and $(cyclopentadienyl)_2M(CH_3)^{m+}$, wherein M is a transition metal. Preferably, for many battery applications, the cation is an alkali metal cation; most preferably, the cation is a lithium cation.

Suitable monovalent or divalent organic R groups include a fluorine atom, a hydrocarbon or a fluorinated hydrocarbon group. Preferably, R includes a monovalent or divalent nonfluorinated or fluorinated straight or branched, saturated or unsaturated aliphatic group having 1 to 18 carbon atoms, a cycloaliphatic group of 3 to 12 carbon atoms, a cycloaliphatic-aliphatic group in which the aliphatic group has 1 to 4 carbon atoms, in which the carbon chain of the aliphatic or cycloaliphatic groups are uninterrupted or interrupted by a catenary heteroatom and which the aliphatic or cycloaliphatic group is unsubstituted or substituted by a halogen atom; an aryl or arylaliphatic group, in which said aliphatic group has 1 to 4 carbon atoms, or a reactive group. More preferably, R is a monovalent perfluoroalkyl group of from 1 to 12 carbon atoms, most preferably 1 to 4 carbon atoms. If divalent, a preferred R group is either perfluoroethylene, perfluoropropylene or perfluorobutylene, e.g., $-(CF_2)_n-$, where n=2–4.

Suitable reactive groups may include those groups containing double bonds (e.g., vinyl, allyl, vinylbenzyl, acryloyl or methacryloyl groups) or those groups containing reactive heterocyclic ring structures (e.g., oxirane (epoxy), oxetane, azetidine or aziridine groups). A suitable reactive group may also include those groups containing hydroxyl, amino, isocyanato or trialkylsilyl groups. When the reactive group could interfere with reactions for preparing the desired amide or methide, the reactive group can be protected by reactants that are reversibly bound to it. For example, a double bond may be protected as a dihalo derivative and subsequently dehalogenated.

Examples of suitable R groups containing reactive groups include $CH_2=CH-$, $CH_2=CHO-$, $CH_2=CHCH_2-$, $CH_2=CHCH_2O-$, $CH_2=C(CH_3)-$, $(CH_2=CHCH_2)_2N-$, $(CH_2=CHCH_2)NH-$, $CF_2=CFO-$, $CF_2=CF-$, $CH_2=CHC(O)OCH_2CH_2-$, $CH_2=CH-C_6H_4-$, $CH_2=C(CH_3)C(O)OCH_2CH_2O-$, $CH_2=C(CH_3)C(O)OCH_2CH_2NH-$, $CH_2=CH-C_6H_4-O-$, $c-C_2H_3O-CH_2-$(glycidyl), $HOCH_2CH(OH)CH_2O-$ and $CH\equiv CCH_2-$.

Particularly preferred electrolytes of the invention include methide and amide salts of the formulae:

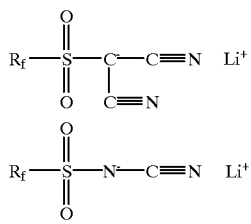

wherein $R_f$ is a perfluoroalkyl group of from 1 to 12 carbon atoms.

The matrix material can be chosen to provide the particular conductivity, viscosity, mechanical strength, and reactivity properties desired for the electrolyte. Suitable matrix materials for preparing electrolyte solutions can be liquid, polymeric, or mixtures of polymer and liquid.

In electrochemical cells including a highly reducing electrode (such as lithium metal) and a liquid matrix material, solvent is preferably present in the matrix material, the solvent preferably including a nonaqueous, polar, aprotic, organic solvent. Such solvents are generally dry, having a water content of less than about 100 ppm, preferably less than about 50 ppm. Examples of suitable aprotic solvents include linear ethers such as diethyl ether, diethylene glycol dimethyl ether, and 1,2-dimethoxyethane; cyclic ethers such as tetrahydrofuran, 2-methyltetrahydrofuran, dioxane, dioxolane, and 4-methyldioxolane; esters such as methyl formate, ethyl formate, methyl acetate, dimethyl carbonate, diethyl carbonate, propylene carbonate, ethylene carbonate, and butyrolactones (e.g. gamma butyrolactone); nitriles such as acetonitrile and benzonitrile; nitro compounds such as nitromethane or nitrobenzene; amides such as N,N-dimethylformamide, N,N-diethylformamide, and N-methylpyrrolidinone; sulfoxides such as dimethyl sulfoxide; sulfones such as dimethylsulfone, tetramethylene sulfone, and other sulfolanes; oxazolidinones such as N-methyl-2-oxazolidinone and mixtures thereof.

Examples of suitable solid matrix materials include polymers and copolymers such as polyethers like poly(ethylene oxide), polyesters, polyacrylates, polyphosphazenes, polysiloxanes, poly(propylene oxide), fluoropolymers (e.g., poly(vinylidene fluoride)), and poly(acrylonitrile), as well as the polymers and copolymers described in Armand et al., U.S. Pat. No. 4,505,997, incorporated herein by reference, and mixtures thereof. The polymers may be used in cross-linked or uncross-linked form and or plasticized. When used in Li batteries, such materials are generally dry, i.e., have a water content less than about 100 ppm, preferably less than about 50 ppm. Mixtures of matrix materials can be employed and are sometimes preferred in tailoring the matrix material's properties to provide optimum performance. In an alternative embodiment, the matrix material may also include a separator in the case where electrolyte is imbibed in the separator.

Salts of the invention can be useful in a number of applications that require or gain advantage from the presence of weakly coordinating anions. For instance, the methide and amide salts of the invention can be useful as conductivity additives, e.g., for coating processes including electrostatic spray coating processes as described in U.S. Ser. No. 08/937,519, expressly incorporated by reference herein, as cationic polymerization initiators or catalysts, as antistatic additives, as surfactants, and as electrolytes (e.g., for use within electrochemical cells including but not limited to battery cells, fuel cells, rechargeable battery cells, capacitors, supercapacitors and electrochemical sensors). The particular electrolyte salts that can be useful, as well as the specific amount of the salt within an electrolytic composition, can depend on a number of factors, including the desired application within which the electrolyte salt will be used.

If the R group is sufficiently large to be hydrophobic, the electrolytic salts of the invention can function as surfactants since the anions will effectively have separate hydrophobic and hydrophilic portions. Such surfactant salts have R groups which have 4 or more carbon atoms, preferably 8 or more carbon atoms. Specifically, surfactant salts aid in the wetting of components with the electrolyte without adversely affecting cell performance.

Conductivities of the electrolyte salts of this invention in typical nonaqueous, polar, aprotic liquid media (e.g., propylene carbonate) are generally in the range of 0.1–20 mS/cm (milliSiemens/cm), at room temperature, preferably greater than 1 mS/cm. The optional solvent may be present at a concentration ranging from about 1 to 95 wt-%.

Batteries and Electrochemical Cells

The invention is also found in an electrochemical cell utilizing an electrolyte which contains one or more salts of the formula

and a matrix material, wherein y, R, Q, X, n and $M^{m+}$ are as defined above, an anode, and a cathode.

The methide or amide electrolyte salts above defined can preferably be employed in a battery electrolyte composition at a concentration such that the conductivity of the electrolyte composition is at or near its maximum value, although a wide range of other concentrations might also be useful for a range of applications. In general, the concentration of the electrolytic methide or amide salt within a battery electrolyte composition can range from about 0.1M to about 2.0M, and is preferably in a range from about 0.5 to 1.5M, most preferably about 1M.

Specifically, within electrochemical cell applications, particularly useful salts, R and $M^{m+}$ components thereof, can be chosen to be optimal within a specific battery system. The salts are useful for maintaining charge balance within the battery. To form the electrolyte, an electrolyte salt according to the invention can be mixed with a matrix material such that the electrolyte salt is at least partially dissolved or dispersed in the matrix material ("solvent" is in the class of "matrix materials"). Useful and preferred metal cations and matrix materials can depend on the entire construction of the battery, e.g., the cathode, anode, current collector, etc.

In some cases, it may be useful or desirable to add other known conductive salts to a battery electrolyte composition to maximize performance or battery cell properties. Such additional salts can include, but are not limited to, alkali metal, alkaline earth metal, alkyl ammonium and Group IIIB metal (e.g., aluminum) salts of anions such as $NO_3^-$, $BF_4^-$; $PF_6^-$; $AsF_6^-$; $ClO_4^-$; $SbF_6^-$; $R_fSO_3^-$ (in which $R_f$ is a perfluoroalkyl group having between 1 and 12 carbons, preferably between 4 and 8 carbons); a bis-(perfluoroalkylsulfonyl)imide anion of the formula —$N(SO_2R_f)(SO_2R_f^1)$ in which $R_f$ and $R_p^1$ are independently perfluoroalkyl groups having between 1 and 12 carbon atoms, inclusive; an (arylsulfonyl) perfluoroalkylsulfonyl-imide anion of the formula —$N(SO_2R)(SO_2R_f)$ in which R is alkyl or aryl and $R_f$ is as previously described; an anion having a formula selected from the group consisting of $R_{f1}R_{f2}N$ —$(CF_2)_n$—$SO_2$—$X^-$ and

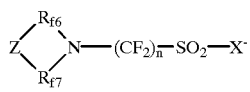

in which $X^-$ is —$O^-$, —$N^-SO_2R_{f3}$, or

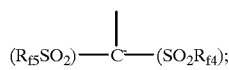

Z is —$CF_2$—, —O—,

or —$SF_4$—; $R_{f1}$ and $R_{f2}$, independently, are —$CF_3$, —$C_mF_{2m+1}$, or —$(CF_2)_q$—$SO_2$—$X^-M^+$; $R_{f3}$, $R_{f4}$, and $R_{f5}$, independently, are —$CF_3$, 13 $C_mF_{2m+1}$, —$(CF_2)_q SO_2$—$X^-M^+$,

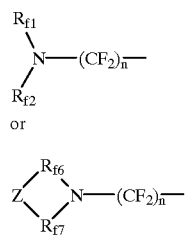

$R_{f8}$ is —$CF_3$, —$C_mF_{2m+1}$, or —$(CF_2)_q$—$SO_2$—$X^-M^+$; $R_{f6}$ and $R_{f7}$, independently, are perfluoroalkylene moieties having the formula —$C_rF_{2r}$—; n is 1–4; r is 1–4; m is 1–12 preferably 1–8; and q is 1–4; (such salts are described by Waddell, et al. in U.S. Pat. No. 5,514,493); a bis-perfluoroalkylsulfonyl methide anion $R_f$—$SO_2$—$C^-(R)$—$SO_2$—$R_f^1$ in which $R_f$ and $R_f^1$, independently, are perfluoroalkyl groups having between 1 and 12 carbon atoms, inclusive, and R is H, Br, Cl, I, an alkyl group having between 1 and 20 carbon atoms, inclusive, aryl, or alkylaryl; and a tris-(perfluoroalkylsulfonyl)methide anion of the formula —$C(SO_2R_f)(SO_2R_f^1)(SO_2R_f^{''})$ in which $R_f$, $R_f^1$, and $R_f^{''}$, independently, are perfluoroalkyl groups having between 1 and 12 carbon atoms, inclusive.

Preferred additional conductive salts include those having a lithium cation and having an anion selected from the group consisting of $PF_6^1$ anion; $ClO_4^-$ anion; $BF_4^-$ anion; a perfluorinated sulfonate anion of the formula $R_{f0}SO_3^-$, in which $R_{f0}$ is a perfluoroalkyl group having from 1 to 8 carbon atoms; a perfluorinated acyclic imide anion of the formula $(R_{f1}SO_2)(R_{f2}SO_2)N^-$, wherein $R_{f1}$ and $R_{f2}$ are each independently a straight or branched perfluoroalkyl group having from 1 to 8 carbon atoms, with $R_{f1}$, and $R_{f2}$ having a total of up to 10 carbon atoms; a perfluorinated cyclic imide anion of the formula:

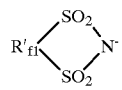

in which $R'_{f1}$ is a perfluoroalkylene moiety of 2 to 4 carbon atoms, optionally substituted by a straight or branched perfluoroalkyl group of 1 to 2 carbon atoms, with $R'_{f1}$ having a total of up to 6 carbon atoms; and a tris (perfluoroalkylsulfonyl) methide anion of the formula $^-C(SO_2R_{f13})(SO_2R_{f14})(SO_2R_{f15})$, in which $R_{f13}$, $R_{f14}$, and $R_{f15}$ independently are perfluoroalkyl groups having between 1 and 8 carbon atoms.

Most preferred additional conductive salts include $LiBF_4$, $LiAsF_6$, $LiClO_4$, $LiPF_6$, $LiNO_3$, $C_4F_9SO_3Li$, $C_8F_{17}SO_3Li$, $(CF_3SO_2)_2NLi$, $(C_2F_5SO_2)_2NLi$, $(C_8F_{17}SO_2)(CF_3SO_2)NLi$, $(C_8F_{17}SO_2)(C_2F_5SO_2)NLi$, $(CF_3SO_2)_2NNa$, $[(CF_3SO_2)_2N]_3Al$, $(CF_3)_2NC_2F_4SO_3Li$, $(CF_3SO_2)_3CLi$, $C_6H_5SO_2NLiSO_2CF_3$, $((CF_3)_2NC_2F_4SO_2)_2NLi$ and mixtures thereof.

A preferred chemical power source of the present invention relates to a battery that includes at least one cathode, at least one anode, a separator and liquid electrolyte comprising one or more amide or methide salts of the present invention and aprotic solvents.

The electrodes (i.e., anode and cathode) of, for example, a lithium battery generally consist of a metallic foil and particles of active material blended with a conductive diluent such as carbon black or graphite bound into a plastic material binder. Typical binders include polytetrafluoroethylene, polyvinylidene fluoride, ethylene-propylene-diene (EPDM) terpolymer, and emulsified styrene-butadiene rubber (SBR), and the binder may be cross-linked. The binder may also be, for example, a solid carbon matrix formed from the thermal decomposition of an organic compound. The metallic foil or composite electrode material is generally applied to an expanded metal screen or metal foil (preferably aluminum, copper or nickel) current collector using a variety of processes such as coating, casting, pressing or extrusion. In polymer electrolyte batteries, the polymer electrolyte can act as the active material binder.

Examples of suitable anode (negative electrode) materials include but are not limited to lithium metal, lithium metal alloys, sodium metal, carbon-based materials such as graphite, coke, carbon fiber, pitch, transition metal oxides (such as $LiTi_5O_{12}$ and $LiWO_2$), and lithiated tin oxide. In the case of lithium ion batteries, the lithium may be intercalated into a host material such as carbon (i.e., to give lithiated carbon) or carbon alloyed with other elements (such as silicon, boron and nitrogen), a conductive polymer, or an inorganic host that is intercalatable (such as $Li_xTi_5O_{12}$.) The material comprising the anode may be carried on foil (e.g., nickel and copper) backing or pressed into expanded metal screen and alloyed with various other metals.

Examples of suitable cathode (positive electrode) materials include but are not limited to graphite, amorphous carbon, $Li_xCoO_2$, $Li_xNiO_2$, Co-doped $Li_xNiO_2$, $Li_xMn_2O_4$, $Li_xMnO_2$, $V_2O_5$, $V_6O_{13}$, $LiV_3O_8$, $Ba_2SmNiO_5$, $SmMnO_3$, $Sm_3Fe_5O_{12}$, $EuFeO_3$, $EuFe_5O_{12}$, chromium doped manganese spinel, $EuMnO_3$, $LaNiO_3$, $La_2CoO_4$ and $LaMnO_3$ (including the charged and discharged forms of these materials), and conducting polymers such as polypyrrole, polysulfides and polyvinylferrocene. In primary batteries, the cathode can be fluorinated carbon (e.g., $(CF_x)_n$), $SO_2Cl_2$, $Ag_2CrO_4$, sulfur, polysulfide, and an $O_2$ or $SO_2$ electrode.

Lithium batteries and supercapacitors usually contain a separator to prevent short-circuiting between the cathode and anode. The separator usually consists of a single-ply or multi-ply sheet of microporous polymer (typically polyolefin, e.g., polyethylene, polypropylene, or combinations thereof) having a predetermined length and width and having a thickness of less than 10 mils (0.025 cm). For example, see U.S. Pat. Nos. 3,351,495 (Larsen et al.), 4,539,256 (Shipman et al.), 4,731,304 (Lundquist et al.) and 5,565,281 (Yu et al.). The pore size in these microporous membranes, typically about 5 microns in diameter, is sufficiently large to allow transport of ions but is sufficiently small to prevent cathode/anode contact, either directly or from particle penetration or dendrites which can form on the electrodes.

The invention includes primary and secondary batteries. In primary batteries, the cathode could be fluorinated carbon $(CF_x)_n$, $SO_2$, $SO_2Cl_2$, or $Ag_2CrO_4$.

Compounds

The invention includes novel methide salts of the formula:

In this formula, y is 1 or 2, R is a fluorine atom or a perfluorinated hydrocarbon group, and $M^{m+}$ is a cation having a valence of m.

Suitable cations, $M^{m+}$, include alkali metal cations (e.g., $Li^+$, $Na^+$, $K^+$ and $Cs^+$), alkaline earth metal cations (e.g., $Mg^{2+}$, $Ca^{2+}$, $Sr^{2+}$ and $Ba^{2+}$), Group IIIA cations (e.g., $Al^{3+}$), transition metal cations (e.g., $Fe^{3+}$, $Fe^{2+}$, $Zn^{2+}$, $Ti^{4+}$ and $Cu_{2+}$), rare earth metal cations (e.g., $Ce^{4+}$ and $La^{3+}$), alkylammonium cations (i.e., $R_4N^+$, where R is independently alkyl, preferably having from 1 to 4 carbon atoms, aryl or hydrogen), sulfonium ions (i.e., $R_3S^+$), iodonium ions (i.e., $R_2I^+$), phosphonium ions ($R_4P^+$) and protons (i.e., $H^+$). Suitable cations also include organometallic cations such as ferrocenium cation, cyclopentadienyl (arene)$M^{m+}$, (arene)M$(CO)_3^{m+}$, $(arene)_2M^{m+}$ and $(cyclopentadienyl)_2M(CH_3)^{m+}$, wherein M is a transition metal. Preferably, the cation is an alkali metal cation. Most preferably, the cation is a lithium cation.

Suitable monovalent or divalent perfluorinated organic R groups include divalent perfluorinated straight or branched, saturated or unsaturated aliphatic group having 1 to 18 carbon atoms, a perfluorinated cycloaliphatic group of 3 to 12 carbon atoms, a perfluorinated cycloaliphatic-aliphatic group in which the aliphatic group has 1 to 4 carbon atoms, in which the carbon chain of the aliphatic or cycloaliphatic groups are uninterrupted or interrupted by a heteroatom and which the aliphatic or cycloaliphatic group is unsubstituted or substituted by a halogen atom or a reactive group; a perfluorinated aryl or arylaliphatic group, in which said aliphatic group has 1 to 4 carbon atoms. More preferably, R is a perfluorinated alkyl, alkylene, cycloalkyl or aralkyl group in which alkyl, cycloalkyl or aryl group is unsubstituted or substituted by a polymerizable reactive group Preferably, R is a perfluorinated alkyl group of 1 to 12 carbon atoms and, most preferably, a perfluorinated alkyl group of 1 to 4 carbon atoms. Especially preferred R groups are perfluorinated hydrocarbons selected from the group consisting of perfluoromethyl and perfluorobutyl.

Suitable reactive groups may include those groups containing double bonds (e.g., vinyl, allyl, vinylbenzyl, acryloyl or methacryloyl groups) or those groups containing reactive heterocyclic ring structures (e.g., oxirane (epoxy), oxetane, azetidine or aziridine groups).

Particularly preferred methide compounds of the invention include:

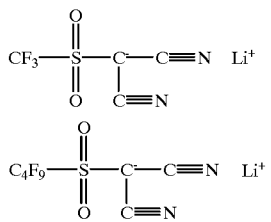

The invention includes novel amide salts of the formula

In this formula, y is 1 or 2, and Q is a linking group selected from $—SO_2—$ and $—C(O)—$. R is as defined above. Finally, $M^{m+}$ is a cation having a valence of m.

Suitable cations, $M^{m+}$, include alkali metal cations (e.g., $Li^+$, $Na^+$, $K^+$ and $Cs^+$); alkaline earth metal cations (e.g., $Mg^{2+}$, $Ca^{2+}$, $Sr^{2+}$ and $Ba^{2+}$); Group IIIA cations (e.g., $Al^{3+}$); transition metal cations (e.g., $Fe^{3+}$, $Fe^{2+}$, $Zn^{2+}$, $Ti^{4+}$ and $Cu^{2+}$); rare earth metal cations (e.g., $Ce^{4+}$ and $La^{3+}$); alkylammonium cations (i.e., $R_4N^+$, where R is independently alkyl, preferably having from 1 to 4 carbon atoms, aryl or hydrogen); sulfonium cations (i.e., $R_3S^+$); iodonium cations (i.e., $R_2I^+$); phosphonium cations (i.e., $R_4P^+$) and protons (i.e., $H^+$). Suitable cations also include organometallic cations such as ferrocenium cation, cyclopentadienyl (arene) $M^{m+}$, $(arene)M(CO)_3^{m+}$, $(arene)_2M^{m+}$, (cyclopentadienyl)$_2M(CH_3)^{m+}$, onium cations such as diaryliodium or triarylsulfurium, wherein M is a transition metal. Preferably, the cation is an alkali metal cation. Most preferably, the cation is a lithium cation.

Especially preferred amide compounds include:

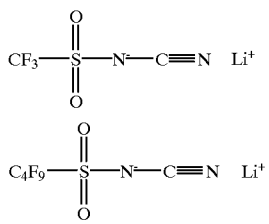

The amide and methide salts, as stated above, can contain reactive moieties which allow the dimerization, trimerization, oligomerization, grafting or polymerization of such reactive amide or methide salts. These compounds can be reacted by known polymerization or grafting reactions methods to create solid, polymerized or copolymerized materials with pendant amide or methide salt groups.

Moreover, certain methide and amide salts are preferred embodiments of the present invention which include polymerizable groups. These include methide salts of the formula

wherein y is 1 or 2;

R is a halogenated or non-halogenated polymerizable group;

Q is a linking group; and $M^{m+}$ is a cation having a valence of m; and amide salts of the formula

wherein y is 1 or 2;

R is a halogenated or non-halogenated polymerizable group; and $M^{m+}$ is a cation having a valence of m.

Synthesis

In general, the above-described cyano-containing methides and amides containing perfluorosulfonylalkyl groups can be prepared from the reaction of fluoroalkylsulfonyl fluorides, $R_fSO_2F$, with anhydrous malononitrile and cyanamide, respectively, in the presence of a non-nucleophilic base. This synthetic procedure is described in Scheme 1 of U.S. patent application Ser. No. 08/577,425 for making (bis)fluoroalkylsulfonylimides, which is herein incorporated by reference, wherein either the malononitrile or the cyanamide is substituted for the fluoroalkylsulfonamide. The intermediate non-nucleophilic base cation-containing methide or amide salt can be converted to the desired cation salt (typically lithium) via standard methods known in the art. Obvious variations of this synthetic procedure can be used to make methides and amides containing other R groups, as described in U.S. patent application Ser. No. 08/937,519.

Synthesis of Methides

Preferred methides can be prepared according to the procedure shown below

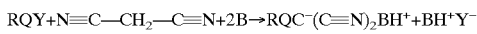

Synthesis of Amides

Preferred amides can be prepared according to the procedure shown below:

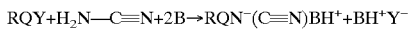

where Y is a leaving group such as halogen or tosylate, and B is a non-nucleophilic base such as a tertiary amine, e.g. triethylamine or pyridine. The reaction can also use inorganic bases, such as, for example, solid anhydrous alkali metal carbonates.

Perfluoroalkylsulfonyl fluorides can be prepared by a variety of methods known in the chemical art, and as described, for example, in U.S. Pat. Nos. 3,542,864; 5,318,674; 3,423,299; 3,951,762; 3,623,963; 2,732,398; S. Temple, *J. Org. Chem.*, 33(1), 344 (1968); and D. D. DesMarteau, *Inorg. Chem.*, 32, 5007 (1993), all of which are incorporated herein by reference.

The invention is illustrated further by, but is not intended to be limited to, the following examples.

EXAMPLES

Note: All electrolyte salt samples were stored and handled in a nitrogen- or argon-filled dry box (Vacuum Atmospheres Inc.) to prevent contamination by water.

Preparation of Electrolyte Salts

A solution containing 10 g of cyanamide, 120 mL of dry triethylamine and 120 mL of dry acetonitrile (available from Aldrich Chem. Co., Milwaukee, Wis. as anhydrous acetonitrile in a SURE SEAL™ bottle) was placed in a non-stirred bomb reactor. The reactor was sealed, and a molar excess of $CF_3SO_2F$ (>35 g, available from 3M Company, St. Paul, Minn.) was carefully added, making sure that the temperature did not rise too quickly. The sealed reactor with its contents was then placed on a shaker and the contents were allowed to react overnight.

Next day, the reactor was opened, and the resulting brown mixture was transferred to a flask and was stripped of solvent using reduced pressure distillation. About 250 mL of methylene chloride was added to the residue, and the resulting solution was washed twice with 250 mL aliquots of deionized water. The organic phase was separated and the solvent was removed by reduced pressure distillation. The acidic residue was then neutralized and solubilized by stirring for 40 minutes in 300 mL of water containing 15 g of LiOH.H$_2$O to form the aqueous solution of the crude lithium salt.

Water was then removed from the lithium salt solution using reduced pressure distillation, and about 100 mL of methyl t-butyl ether (MTBE) was added to dissolve the residue. Insolubles were removed by filtration, and the filtrate was dried over anhydrous MgSO$_4$ for a day. The solution was then filtered to remove the drying agent, decolorizing carbon was added, and the solution was heated to boiling for 3 minutes followed by cooling to room temperature. The carbon was then filtered off, resulting in a pale yellow filtrate. About 200 mL of toluene was added to the ether solution, and both solvents were removed using reduced pressure distillation. Another two 200 mL aliquots of toluene were added to and distilled from the flask, leaving behind a white powder in the flask. This powder was dried at 100° C. in a vacuum oven to produce 23.9 g of $CF_3SO_2N$(Li)CN (56% yield), whose structure was confirmed by mass spectroscopy and $^{19}F$ NMR analysis ($CD_3CN$, δ=−77.77(s) ppm).

$C_4F_9SO_2N$(Li)CN

A solution containing 4.0 g of cyanamide, 75 mL of anhydrous acetonitrile and 50 mL of triethylamine was prepared in a flask by stirring under a nitrogen blanket at a temperature of 0° C. Then 32 g of $C_4F_9SO_2F$ (88% pure, the remaining 12% being non-functional inert material, available from 3M Company) was added dropwise, and the reaction mixture was warmed to room temperature and stirred overnight.

The next day, the solvent was removed by reduced pressure distillation, the residue was dissolved in methylene chloride, and the resulting solution was washed twice with 250 mL aliquots of deionized water. The organic phase was saved and the solvent was removed by reduced pressure distillation. The acidic residue was then neutralized and solubilized by stirring for 2 hours in 150 mL of water containing 6 g of $LIOH.H_2O$ to form the crude lithium salt aqueous solution.

Water was then removed from the lithium salt solution using reduced pressure distillation, and about 100 mL of MTBE was added to dissolve the residue. Insolubles were removed by filtration, and the filtrate was dried over anhydrous $MgSO_4$ for a day. The solution was then filtered to remove the drying agent, decolorizing carbon was added, and the solution was heated to boiling for a few minutes followed by cooling. The carbon was then filtered off, and about 200 mL of toluene was added to the ether solution, and both solvents were removed using reduced pressure distillation, leaving behind a white powder in the flask. This powder was dried at 100° C. in a vacuum oven to produce 9.7 g of $C_4F_9SO_2N$(Li)CN (26% yield), whose structure was confirmed by mass spectroscopy and $^{19}F$ NMR analysis ($CD_3CN$, 376 MHz, δ−80.5(t/t) 3F, δ−112.5(t) 2F, δ−120.8 (m) 2F, δ−125.4(m) 2F).

$CF_3SO_2C$(Li)$(CN)_2$

First, the pyridinium salt intermediate was prepared using the following procedure. To a 500 mL flask vented with nitrogen was added 200 g of anhydrous pyridine via cannula (a "cannula" is a long double-ended syringe needle for transferring liquids from a pressurized container sealed with a septum). Then 66 g of malononitrile (available from Aldrich Chem. Co.) was gently heated to past its melting point and was added to the pyridine-containing flask in a similar manner, causing a red solution to form. The red solution was transferred to an evacuated 600 mL stirred monel Parr bomb reactor. The reactor and its contents were chilled to a temperature of 0° C. with stirring, and $CF_3SO_2F$ was slowly added, controlling the addition rate so that the temperature in the reactor never exceeded 10° C. When the exotherm was over, the addition of $CF_3SO_2F$ continued until the pressure reached 50 psi (2600 torr), as measured at 5° C. The reactor and its contents were then heated to 50° C. with stirring for 4 hours, during which time the pressure in the reactor dropped from 160 psi (8300 torr) to 120 psi (6200 torr). The contents of the reactor were then stirred overnight as the reactor was allowed to cool to room temperature. The next day, the reactor was vented and was heated to 70° C. under vacuum for 45 minutes to remove the volatile products. The residue remaining in the reactor was extracted three times with 200 mL aliquots of deionized water to give 260 g of crude product consisting of a dark red oil (94% yield), believed to be the crude pyridinium salt intermediate, $C_5H_5NH^+$−$C(CN)_2(SO_2CF_3)$.

The pyridinium salt intermediate was converted to the desired purified lithium salt through a cesium salt intermediate using the following procedure. To a separatory funnel was added 56 g of pyridinium salt intermediate, 500 mL of MTBE and 500 mL of 2M aqueous $H_2SO_4$. After shaking, the resulting dark mixture formed two liquid phases, which were separated, and the organic phase was saved. Anhydrous $K_2CO_3$ was mixed overnight with the organic phase to dry and neutralize the contents of the phase, resulting next day in the formation of a brown sticky precipitate. The phase with precipitate was filtered and the resulting solids washed with 300 mL of acetonitrile. The two filtrates were combined, the solvents were removed by reduced pressure distillation, and the residue was dissolved in about 100 mL of deionized water. Then 30 g of CsF (available from Aldrich Chem. Co.) was added, and the resulting solution was recrystallized. A pink solid formed, believed to be the cesium salt intermediate of the desired product. The cesium salt was recrystallized twice more from water, but the pink color remained. A further purification attempt was done by dissolving all of the resulting pink crystals in about 30 mL of acetonitrile and passing the resulting solution through a column of basic alumina using MTBE as the mobile phase. Extra MTBE was also used to flush the column. The MTBE samples were combined, stripped of solvent using reduced pressure distillation, and the residue was dissolved in 50 mL of deionized water. To this aqueous solution was added 10 g of conc. $H_2SO_4$ and 50 mL of MTBE. The resulting two phases were mixed and the organic phase was isolated. A molar excess of $Li_2CO_3$ was added to neutralize the dicyanomethide acid formed in the organic phase. The resulting lithium salt solution in MTBE was then filtered and concentrated by reduced pressure distillation. Toluene was added to azeotrope the remaining water and MTBE. Drying of the wet solid overnight at 80° C. in a vacuum oven produced 3.7 g of a white powder, $CF_3SO_2C$(Li)$(CN)_2$, whose structure was confirmed by mass spectroscopy and $^{19}F$ NMR analysis ($CD_3CN$, 376 MHz, δ−79.86(s)).

$C_4F_9SO_2C$(Li)$(CN)_2$—Using Triethylamine Route

To a dry flask purged with nitrogen was added 4.0 g of malononitrile, 75 mL triethylamine and 65 mL of acetonitrile. The resulting solution was stirred and cooled to 0° C., then 24 g of $C_4F_9SO_2F$ was added dropwise and the solution was stirred overnight while warming to room temperature. The remaining synthetic procedure followed was the same as that described for the preparation of $CF_3SO_2N$(Li)CN except that, in this case, the carbon treatment did not remove much of the color from the product. Drying the resulting light brown powder under vacuum at 50° C. produced 17.2 g of $C_4F_9SO_2C$(Li)$(CN)_2$ (79% yield), whose structure confirmed by MS and $^{19}F$ NMR ($CD_3CN$, 376 MHz, δ−80.4 (t/t) 3F, δ−113.3 (t) 2F, δ−120.5 (m) 2F, δ−125.3 (m) 2F).

$C_4F_9SO_2C$(Li)$(CN)_2$—Using Potassium Carbonate Route 10.5 g of $K_2CO_3$ was placed in a dry tared 200 mL flask and was heated under vacuum with a heat gun until the reading on the vacuum meter returned to normal (i.e., vacuum created), indicating that all of the water was removed from the $K_2CO_3$. The flask was allowed to cool and then was weighed to accurately determine the amount of anhydrous $K_2CO_3$ remaining in the flask. 4.0 g of molten malononitrile (gently warmed using a heat gun) was added to the flask, followed by 75 mL of anhydrous acetonitrile and 20 g of $C_4F_9SO_2F$. This mixture was then stirred and heated to reflux overnight.

The next day, the solids were removed by filtration and the solvent was removed from the filtrate by reduced pressure distillation. The resulting brown residue was dissolved in water, was recrystallized twice from water, and was washed with a little isopropyl alcohol. The now yellow-brown solid was dissolved in a small amount of MTBE and was passed through a column of basic alumina using MTBE as the mobile phase. A pale yellow solution was collected, which was washed with a mixture of 100 mL of deionized water and 20 g of concentrated $H_2SO_4$. The washed MTBE solution was neutralized with $Li_2CO_3$, and the neutralized solution was filtered and concentrated by removing the solvents by reduced pressure distillation. Toluene was then added, followed by more reduced pressure distillation. The resulting white powder was dried at 75° C. for 6 hours in a vacuum oven to give 4.5 g of the purified product (21% yield).

$LiN(SO_2C_2F_5)_2$

Lithium bis(perfluoroethylsulfonyl)imide was prepared as described in Example 3 of U.S. Pat. No. 5,652,072, which is hereby incorporated by reference herein. The structure of the product was confirmed by $^1H$ and $^{19}F$ NMR spectroscopy, which indicated that the purity of the electrolyte salt was 99.9% by weight.

$LiN(SO_2CF_3)_2$

The electrolyte salt $LiN(SO_2CF_3)_2$ used in the examples is commercially available in high purity from 3M Company, St. Paul, Minn., as FLUORAD™ HQ-115 Lithium Trifluoromethanesulfonimide Battery Electrolyte.

$LiPF_6$

High purity, battery grade $LiPF_6$ electrolyte salt was purchased from Hashimoto Chemical Co., Ltd. through Biesterfeld Inc., a U.S. distributor.

$CH_2=CH-C_6H_4-SO_2C(Li)(CN)_2$

In a 3-necked 250 mL round bottom flask, 2.3 g of malononitrile (66 g/mol, 0.035 mol) was dissolved in about 20 mL of anhydrous acetonitrile under $N_2$ atmosphere. In a dry 100 mL flask, 8.0 g of p-styrenesulfonyl chloride (203 g/mol, 0.0395 mol) was dissolved in 20 mL anhydrous acetonitrile. This second solution was then added to the contents of the 250 mL round bottom flask via cannula under $N_2$ atmosphere, and an exotherm resulted. The reaction mixture in the round bottom flask was allowed to cool in an ice bath with stirring, and 25 mL of triethylamine was added dropwise via syringe. This reaction mixture was then stirred for 48 hours after it was allowed to warm to room temperature.

After removing the solvents by reduced pressure distillation using a Rotovap™ rotary evaporator, a solution consisting of 5 g LiOH $H_2O$ in 100 mL deionized water was added to the reaction mixture. The resulting dark aqueous solution became homogeneous after stirring and periodically scraping material from the surface of the flask. Using the Rotovap™ rotary evaporator, water was removed from the solution until about half of the original solution volume remained. The solution was acidified with 25 g concentrated sulfuric acid, and more water was added to increase the total solution volume to about 100 mL. This acidified solution was then mixed with methylene chloride to extract the organic contents. Using the Rotovap™ rotary evaporator, the methylene chloride was removed from the resulting solution, and the residual brown oil was dissolved with heating in a mixture consisting of 100 mL deionized water and 6 g CsCl to form an aqueous brown solution. A spatula of carbon black was added to the solution, the mixture was filtered and filtrate was recrystallized. Solids were isolated and the recrystallization process from water was repeated two more times. The resulting beige powder was dissolved in a mixture of 100 mL water and 20 g concentrated sulfuric acid, and the acidified product was extracted into 150 mL of methyl t-butyl ether (MTBE). The MTBE phase was isolated and neutralized with a calculated molar excess of $Li_2CO_3$, adding 25 mL of tetrahydrofuran (THF) to ensure that the salt would stay in solution. After neutralization the pale yellow product solution was filtered to remove the excess $Li_2CO_3$. Using the Rotovap™ rotary evaporator, solvent was removed from the filtrate. Once the solution volume was reduced to about half, 50 mL of toluene was added as an azeotroping agent. After drying, 4.1 g of nearly white powder was obtained (49% yield).

IR: $\nu_{CN}$=2223, 2195 cm$^{-1}$

1-H NMR: d(CD3CN)=5.39 (d, J=11 Hz, 1H), 5.93 (d, J=17 Hz, 1H), 6.81(dd, J=17,11 Hz, 1H), 7.59 (dd, J=6.6, 1.7 Hz, 2H), 7.75 (dd, J=6.6, 1.7 Hz, 2H) ppm MS (negative ion direct ionization): $C_{11}H_7N_2SO_2$[M-Li]m/e=231.0234, found; 231.02337, calculated.

Homopolymer of $CH_2=CH-C_6H_4-SO_2C(Li)(CN)_2$

A solution was prepared consisting of 100 mL THF, 4.0 g of $CH_2=CH-C_6H_4-SO_2C(Li)(CN)_2$ and 0.038 g AIBN (2,2'-azobisisobutyronitrile). This solution was heated to reflux and stirred under $N_2$ atmosphere overnight, precipitating a gel-type polymer. The solvent was decanted away, and a mixture of 100 mL THF and 5 mL deionized water was added to the remaining polymer. The resulting mixture was heated to reflux and stirred for 15 minutes to dissolve any unreacted monomer. The solvent was decanted and the remaining solids were dissolved in 125 mL of deionized water with heating and stirring. Undissolved particles were removed by passing the solution through a plug of glass wool. Solvent was removed from the filtrate using a Rotovap™ rotary evaporator to obtain a pale yellow oil. The oil was twice washed with 150 mL aliquots of toluene to yield 3.1 g of the desired homopolymer salt.

GPC analysis of polymer: $M_w$=68700, $M_n$=64000.

$T_g$: about 127° C. by DSC.

Test Methods

Ionic Conductivity

Conductivity measurements for liquid electrolytes were generally made using a 1 molar (1M) electrolyte derived from carefully purified and dried components. The 1M electrolyte was made by dissolving 10 millimoles of electrolyte salt in 10 mL of a 50/50 (vol) mixture of propylene carbonate (PC)/1,2-dimethoxyethane (DME) or ethylene carbonate (EC)/dimethyl carbonate (DMC). 10 mL of the resulting electrolyte was placed in a glass container with a conductivity cell having K=1.0/cm (Model No. 3403, available from YSI Inc., Yellow Spring, Ohio), all kept in a dry box before use. During all times, water contamination in the electrolyte was kept below 30 ppm, as determined by Karl Fischer titration. Impedance response was then measured in milli-Siemens per square centimeter (mS/cm) using a PAR Model 273 potentiostat/galvanometer (available from EG&G Princeton Applied Research, Princeton, N.J.), equipped with a frequency response analyzer (Model 1260, available from Schlumberger, Billerica, Mass.). The impedance response for each cell was measured using an AC signal of 5–10 mv over a frequency response of 100,000 to 1 Hz, using Model 398 Electrochemical Software (available from EG&G Princeton Applied Research). The conductivity was then calculated from the impedance response.

Repassivation Potential

The repassivation potential of the candidate salt was measured using a cyclic voltammetry test employing aluminum as a working electrode, using the technique generally described in Bard and Faulkner, Electrochemical Methods: Fundamentals and Applications, John Wiley and Sons, New York, 1980, pp. 350–353. The repassivation potential is an excellent predictor of the degree of corrosion to be expected when aluminum is used in an electrode, especially as a current collector.

For each cyclic voltammetry measurement, a three-electrode cell was used, having aluminum as the working electrode, metallic lithium as the reference electrode and metallic lithium as the auxiliary electrode. The aluminum electrode consisted of a 99.9% pure aluminum rod inserted into a polytetrafluoroethylene sleeve to provide a planar electrode having an area of 0.07 $cm^2$. Prior to running each cyclic voltammetry test, the native metal oxide layer was removed from the aluminum electrode by polishing the electrode with 3 $\mu$m aluminum oxide paper using heptane as a lubricant. A lithium wire inserted in a luggin glass capillary served as a reference electrode, and a 10 $cm^2$ platinum flag was used as the auxiliary electrode.

After polishing, the three electrodes and a glass cell for holding the electrolyte were all placed in an oxygen- and moisture-free dry box, and the three electrodes were connected to a potentiostat. Each electrolyte salt to be evaluated was dissolved at 1M concentration in a 1:1 (vol) blend of ethylene carbonate:dimethyl carbonate to form the test electrolyte (containing less than 50 ppm water, as determined by Karl Fischer titration), and 10 mL of each test electrolyte was placed in the glass cell. A scan at the rate of approximately 1 mV/sec was taken from 1 V up to at least 5 V (vs. the reference electrode), followed by gradually returning the potential to 1 V, and the current was measured as a function of voltage potential. The repassivation potential was defined as that voltage at which the measured current of the hysteresis loop fell precipitously back to a value close to the currents measured during the early part of the forward scan (i.e., the point of inflection on the curve).

Redox Stability

The redox potential of the candidate salt was measured using a cyclic voltammetry test employing a glassy carbon electrode. The redox potential is an excellent predictor of the electrochemical stability of the salt in the electrolyte—the higher the potential, the more stable the salt.

For each cyclic voltammetry measurement, the same three-electrode cell and test procedure was used as described in the just-described repassivation potential test procedure, except that a glassy carbon rod was substituted for the aluminum working electrode. Analogous to the repassivation potential, the redox potential was defined as that voltage at which the measured current of the hysteresis loop fell precipitously back to a value close to the currents measured during the early part of the forward scan (i.e., the point of inflection on the curve). All electrolyte salt measurements were made at 1 M in 50/50 (vol) ethylene carbonate/dimethyl carbonate.

Chronoamperometry Test

The chronoamperometry test was run (1) to measure residual current density as a function of applied voltage and time and (2) to determine total charge passed during the voltage pulse. Again this test was run using the same electrode cell setup described in the repassivation test procedure, being careful to exclude both water and air from the cell. The aluminum electrode was also polished as described in this procedure. Current vs. time was measured was measured at two different voltage pulses over a period of 1 hour, with the applied voltage of 4.2 V. All electrolyte salt measurements were made at 1 M in 50/50 (vol) ethylene carbonate/dimethyl carbonate.

For stability against corrosion, the current after the 1 hour pulse should fall to less than 5 $\mu$A/$cm^2$.

Examples 1–4 and Comparative Examples C1–C3

Cyano-substituted perfluoroalkylsulfonyl amide and methide electrolyte salts of this invention (Examples 1–4) were compared in a battery electrolyte solution to state-of-the-art electrolyte salts (Comparative Examples C1–C3) for ionic conductivity and aluminum repassivation potential. The battery electrolyte solution consisted of a 1M solution of the test electrolyte salt in a dry solvent blend of 50:50 (volume) propylene carbonate:dimethoxyethane. Results of these measurements are shown in Table 1.

TABLE 1

| Ex. Electrolyte salt | Ionic Conductivity (mS/cm) | Al Repassivation Pot. (V, vs. Li/Li$^+$) |
|---|---|---|
| 1 $CF_3SO_2N(Li)CN$ | 7.2 | <4.2 |
| 2 $C_4F_9SO_2N(Li)CN$ | 5.6 | >4.2 |
| 3 $CF_3SO_2C(Li)(CN)_2$ | 12.5 | 4.7 |
| 4 $C_4F_9SO_2C(Li)(CN)_2$* | 8.3 | >5 |
| C1 $LiN(SO_2CF_3)_2$ | 12 | 3.7 |
| C2 $LiN(SO_2C_2F_5)_2$ | 9.5 | 4.4 |
| C3 $LiPF_6$ | 15 | >5 |

*made using the triethyl amine route

The data in Table 1 show that in general the cyano-substituted perfluoroalkylsulfonyl amide and methide electrolyte salts demonstrate good ionic conductivity, comparable to the state-of-the-art electrolyte salts, with methide electrolyte salts preferable to imide electrolyte salts and trifluoromethylsulfonyl electrolyte salts preferable to perfluorobutylsulfonyl electrolyte salts. With the exception of $CF_3SO_2N(Li)CN$ and $LiN(SO_2CF_3)_2$, aluminum repassivation potential was good for all electrolyte salts, which would predict low corrosion rates for aluminum current collectors used in lithium ion batteries.

Example 5

Chronoamperometry experiments were run to measure the corrosion against a polished aluminum surface exhibited 1M battery electrolyte solutions of $CF_3SO_2N(Li)CN$ and $C_4F_9SO_2N(Li)CN$. The voltage was held constant at 4.2 V, and the resulting current was measured as a function of time. $CF_3SO_2N(Li)CN$ produced a large current due to the corrosion of aluminum, while $C_4F_9SO_2N(Li)(CN)_2$, a larger molecule, was much less corrosive. In fact, the corrosion current for $C_4F_9SO_2N(Li)CN$ was only slightly higher than that measured for $LiN(SO_2C_2F_5)_2$, a commercial imide battery electrolyte salt.

Example 6

$CF_3SO_2C(Li)(CN)_2$ and $C_4F_9SO_2C(Li)(CN)_2$ were measured for redox stability and were both found to be electrochemically stable against glassy carbon above the normal operating voltage of a typical lithium ion cell. $CF_3SO_2C(Li)(CN)_2$ did not oxidize below 4.6 V (vs. Li/Li$^+$), while $C_4F_9SO_2C(Li)(CN)_2$ was even more stable and did not oxidize below 4.7 V.

Example 7

The ionic conductivity of a solid polymer electrolyte containing a dicyano-substituted perfluoroalkylsulfonyl methide electrolyte salt was determined.

A formulation having a lithium:oxygen atomic ratio of 1:10 was prepared by dissolving 1.0 g of $C_4F_9SO_2C(Li)(CN)_2$ and 1.2 g of polyethylene oxide polymer (mol. wt. about 900,000, available from Aldrich Chemical Co.) in 25 mL of $CH_3CN$. The resulting viscous formulation was coated onto a 3M silicone-coated polypropylene release liner using a 6 inch (15 cm) bladed coater to form a coating approximately 40 mils (1000 microns) thick. The wet coating was allowed to air-dry for 1 hour under ambient conditions, then was vacuumed dried for 5 hours at 100° C. to form an electrolyte film having a thickness of approximately 4 to 5 mils (100 to 125 microns). A cell was then constructed by placing the freshly made electrolyte film between two stainless steel electrodes, each having a diameter of 2.5 cm. The cell was then inserted into a cell holder kept in a dry box, and conductivity was measured in mS/cm using the same measuring instruments as were previously described for the measurement of ionic conductivity for liquid electrolytes. The measured ionic conductivity value was $7.62 \times 10^{-6}$ S $cm^{-1}$ at 25° C., which showed that the dicyano-substituted perfluoroalkylsulfonyl methide electrolyte salt imparted good conductivity to the polyethylene oxide polymer.

Example 8

The ionic conductivity and glass transition temperature of a solid polyethylene oxide electrolyte containing $CH_2=CH-C_6H_4-SO_2C(Li)(CN)_2$ homopolymer electrolyte salt (HPES) was determined.

An electrolyte having an Li:O ratio of 1:10 was prepared by combining 0.57 g of HPES with 1.00 g of $[(CH_2CH_2O)_9CH_2O]_n$ (MW=100,000) and 5 mL of a $CH_3CN:THF:H_2O$ solvent mixture (30:30:40 by volume). (HPES was not soluble in $CH_3CN$ or THF). After shaking overnight, the resulting viscous solution was poured into a small aluminum tray and heated under vacuum at 60° for 17 hours. A semi-amorphous electrolyte was obtained. The electrolyte was cut together with the aluminum tray to form a circular layer having a diameter of 5.0 $cm^2$ and a thickness of 20 mil (500 $\mu$m).

The electrolyte/aluminum layer was placed in a dry-box between two stainless steel electrodes and then held under pressure by a conductivity measurement device. The impedance of this solid polymer electrolyte was measured using the same electrochemical instruments as described in the liquid electrolyte example. The bulk conductivity as calculated from the impedance was $1.10 \times 10^{-7}$ S $cm^{-1}$ at room temperature. The DSC of this electrolyte showed that the $T_g$ was −4.8° C. and the $T_m$ was 15° C.

Example 9

The ionic conductivity of another solid polyethylene oxide electrolyte containing $CH_2=CH-C_6H_4-SO_2C(Li)(CN)_2$ homopolymer electrolyte salt (HPES) was measured.

An electrolyte solution was prepared by combining 1.00 g of HPES with 1.00 g polyethylene glycol monomethyl ether (MW=350; available from Sigma/Aldrich Chem. Co., Milwaukee, Wis.) in 6 mL of a solvent mixture of THF: H2O (50:50 v/v). The solution was coated and tested using the same procedure as described in Example 7, except that drying in the aluminum tray was done at 100° C. for 3 hours prior to measuring. The measured bulk conductivity of the dried clear solid electrolyte was $1.10 \times 10^{-7}$ S $cm^{-1}$ at room temperature.

We claim:

1. An electrolyte comprising at least one salt selected from a group consisting of an N-cyano-substituted amide, an N-cyano-substituted sulfonamide, a dicyano-substituted sulfonyl methide, and a dicyanoacyl methide, and a matrix material.

2. An electrolyte comprising:
   (a) at least one salt of the formula:

wherein:
   y is 1 or 2;
   X is C or N, which when X is C, n is 2 and when X is N, n is 1;
   R is a fluorine atom, a hydrocarbon or a fluorinated hydrocarbon group;
   Q is a linking group; and
   $M^{m+}$ is a cation having a valence of m; and
   (b) a matrix material.

3. An electrolyte of claim 2, wherein Q is a linking group selected from the group consisting of $-SO_2-$ and $-C(O)-$.

4. An electrolyte of claim 2, wherein R is a monovalent or divalent non-fluorinated or fluorinated straight or branched, saturated or unsaturated aliphatic group having 1 to 18 carbon atoms, a cycloaliphatic group of 3 to 12 carbon atoms, a cycloaliphatic-aliphatic group in which the aliphatic group has 1 to 4 carbon atoms, in which the carbon chain of the aliphatic or cycloaliphatic groups are uninterrupted or interrupted by a heteroatom and which the aliphatic or cycloaliphatic group is unsubstituted or substituted by a halogen atom or a reactive group; an aryl or arylaliphatic group, in which said aliphatic group has 1 to 4 carbon atoms; or a reactive group.

5. An electrolyte of claim 2, wherein the salt is of the formula

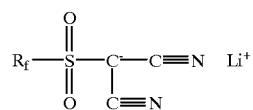

wherein $R_f$ is a perfluoroalkyl group of from 1 to 12 carbon atoms.

6. An electrolyte of claim 5, wherein $R_f$ is perfluoromethyl or perfluorobutyl.

7. An electrolyte of claim 2, where the salt is of the formula

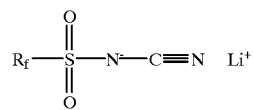

wherein $R_f$ is a perfluoroalkyl group of from 1 to 12 carbon atoms.

8. An electrolyte of claim 7, wherein $R_f$ is perfluoromethyl or perfluorobutyl.

9. An electrolyte of claim 1, which further comprises one or more conductive salts.

10. An electrochemical cell comprising:
   an electrolyte according to claim 1;
   an anode; and
   a cathode.

11. The electrochemical cell of claim 10, wherein the electrolyte comprises a matrix material and at least one salt of the formula $$R\text{—}[Q\text{—}X^-(CN)_n]_y \cdot y/m M^{m+}$$

wherein:
  y is 1 or 2;
  X is C or N, which when X is C, n is 2 and when X is N, n is 1;
  R is a fluorine atom, a hydrocarbon or a fluorinated hydrocarbon group;
  Q is a linking group; and
  $M^{m+}$ is a cation having a valence of m.

* * * * *

UNITED STATES PATENT AND TRADEMARK OFFICE
CERTIFICATE OF CORRECTION

PATENT NO. : 6,294,289 B1
DATED : September 25, 2001
INVENTOR(S) : Fanta, Alan D.

It is certified that error appears in the above-identified patent and that said Letters Patent is hereby corrected as shown below:

Column 4,
Line 10, "atoms," should read -- atoms.--;

Column 5,
Line 37, "CH≡CCH$_2$—." should read -- CH≡CCH$_2$O—. --;

Column 7,
Line 66, "—CF$_3$, 13 C$_m$F$_{2m+1}$, —(CF$_2$)$_q$" should read -- —CF$_3$, C$_m$F$_{2m+1}$, —(CF$_2$)$_q$- --;

Column 8,
Line 28, "PF$_6$' " should read -- PF$_6$- --;

Column 10,
Line 3, "Cu$_{2+}$)," should read -- Cu$^{2+}$), --;
Line 31, "group" should read -- group. --;

Column 14,
Line 5, "—C" should read -- $^-$C --;

Column 15,
Line 52, "LiOH H$_2$O" should read -- LiOH·H$_2$O --; and

UNITED STATES PATENT AND TRADEMARK OFFICE
CERTIFICATE OF CORRECTION

PATENT NO. : 6,294,289 B1
DATED : September 25, 2001
INVENTOR(S) : Fanta, Alan D.

It is certified that error appears in the above-identified patent and that said Letters Patent is hereby corrected as shown below:

Column 21,
Line 5, "2and" should read -- 2 and --.

Signed and Sealed this

Eighteenth Day of June, 2002

*Attest:*

*Attesting Officer*

JAMES E. ROGAN
*Director of the United States Patent and Trademark Office*